United States Patent
Brandstrom (10) Patent No.: US 10,151,729 B2
(45) Date of Patent: Dec. 11, 2018

(54) APPARATUS AND METHOD FOR DETECTION OF IMPERFECTIONS BY DETECTING CHANGES IN FLUX OF A MAGNETIZED BODY

(71) Applicant: Randel Brandstrom, Edmonton (CA)

(72) Inventor: Randel Brandstrom, Edmonton (CA)

( * ) Notice: Subject to any disclaimer, the term of this patent is extended or adjusted under 35 U.S.C. 154(b) by 0 days.

(21) Appl. No.: 15/397,402

(22) Filed: Jan. 3, 2017

(65) Prior Publication Data
US 2018/0188208 A1 Jul. 5, 2018

(30) Foreign Application Priority Data
Dec. 30, 2016 (CA) .................................... 2953295

(51) Int. Cl.
*G01R 33/07* (2006.01)
*G01N 27/83* (2006.01)

(52) U.S. Cl.
CPC ............ *G01N 27/83* (2013.01); *G01R 33/07* (2013.01)

(58) Field of Classification Search
CPC ......... G01N 27/83; G01R 33/07; G01R 33/08
See application file for complete search history.

(56) References Cited

U.S. PATENT DOCUMENTS

| | | | | |
|---|---|---|---|---|
| 4,439,730 A * | 3/1984 | Kauffman | ............... | G01N 27/82 324/232 |
| 4,855,676 A * | 8/1989 | Cecco | ................... | G01N 27/902 324/220 |
| 5,378,362 A * | 1/1995 | Schoepe | ................. | C02F 1/482 210/222 |
| 5,581,037 A * | 12/1996 | Kwun | ..................... | G01N 29/14 324/220 |
| 5,864,232 A * | 1/1999 | Laursen | ............... | G01N 27/902 324/220 |
| 2002/0038199 A1* | 3/2002 | Blemel | ..................... | F17D 5/02 702/183 |
| 2006/0076951 A1* | 4/2006 | Nestleroth | ............. | G01N 27/82 324/220 |
| 2009/0128136 A1* | 5/2009 | Hablizel | ............. | B05B 12/1481 324/207.2 |
| 2009/0139337 A1* | 6/2009 | Owens | ............... | G01N 29/2412 73/622 |

(Continued)

FOREIGN PATENT DOCUMENTS

JP 03077635 A * 5/1991

*Primary Examiner* — Giovanni Astacio-Oquendo
*Assistant Examiner* — Alvaro Fortich
(74) *Attorney, Agent, or Firm* — Adrian D. Battison; Ade & Company Inc.; Ryan W. Dupuis (57) ABSTRACT

An apparatus and method for detection of imperfections by detecting changes in magnetic flux of a magnetized metal body includes a housing carrying first and second magnets for magnetizing the metal body that are located adjacent opposite ends of the housing and a conductor member intermediate the first and second magnets that has a forward end adjacent the metal body and extends outwardly from the metal body to an outer end of the conductor member. At this outer end there is provided a third magnet directing its magnetic field into the conductor member, and at the forward end of the conductor member there is provided a magnetic field sensor to detect changes in magnetic field in the metal body generated by the imperfections as the housing is moved in scanning movement along the metal body.

13 Claims, 5 Drawing Sheets

(56) References Cited

U.S. PATENT DOCUMENTS

| | | | |
|---|---|---|---|
| 2011/0301893 A1* | 12/2011 | Leal Diaz | G01M 3/005 |
| | | | 702/65 |
| 2013/0124109 A1* | 5/2013 | Denenberg | G01N 17/04 |
| | | | 702/35 |
| 2014/0015521 A1* | 1/2014 | Laursen | G01N 27/82 |
| | | | 324/220 |
| 2014/0231637 A1* | 8/2014 | Blemel | G01D 5/35345 |
| | | | 250/227.14 |
| 2016/0379966 A1* | 12/2016 | Chen | H01L 25/16 |
| | | | 257/48 |

* cited by examiner

FIG.1

PRIOR ART

FIG.5

APPARATUS AND METHOD FOR DETECTION OF IMPERFECTIONS BY DETECTING CHANGES IN FLUX OF A MAGNETIZED BODY

FIELD OF THE INVENTION

The present invention relates to an improved method and apparatus for the detection of defects utilizing non-destructive flux leakage techniques in ferrous materials.

BACKGROUND

Flux leakage detection devices are used for detecting defects at or below the surface of objects made of ferromagnetic material, such as metal tubing or piping. Flat, curved or otherwise continuous ferrous bodies as well as continuous welds are also susceptible to inspection by this method. A magnetic field is induced in the body being inspected and a flux leakage sensor is used to detect changes in the magnetic field near the surface of the body. Discontinuities below the surface of a magnetized material are known to cause variations in the magnetic field above its surface and can therefore be detected by the sensor. These devices are therefore passed over the surface area of the body being tested in order to locate defects therein. Prior art methods and devices for flux leakage detection have proven useful but leave much room for improvement in multiple areas.

SUMMARY OF THE INVENTION

According to an aspect of the invention there is provided an apparatus for detecting imperfections in an elongate metal body comprising:

a non-ferromagnetic housing having a surface for location in contact with or immediately adjacent to a surface of the metal body for movement along the body in a scanning action;

a first magnet arranged on the housing adjacent a forward end of the housing at a position closely adjacent the metal body so as to apply a magnetic field in the body;

a second magnet arranged on the housing adjacent a rearward end of the housing at a position closely adjacent the metal body so as to apply a magnetic field in the body;

a ferromagnetic conductor member located on the housing intermediate the first and second magnets having a forward end adjacent the metal body and extending in a direction outwardly away from the metal body to an outer end;

a third magnet located at the outer end of the conductor member so as to direct a magnetic field into the conductor member;

and a magnetic field sensor located at the forward end of the conductor member;

whereby the sensor detects changes in magnetic field in the metal body generated by the imperfections as the housing is moved in scanning movement along the metal body.

According to another aspect of the invention there is provided a method for detecting imperfections in an elongate metal body comprising:

locating a first magnet arranged on a housing adjacent a forward end of the housing at a position closely adjacent the metal body so as to apply a magnetic field within in the body;

locating a second magnet arranged on the housing adjacent a rearward end of the housing at a position closely adjacent the metal body so as to apply a magnetic field within the body;

locating a ferromagnetic conductor member on the housing intermediate the first and second magnets having a forward end adjacent the metal body and extending in a direction outwardly away from the metal body to an outer end;

locating a third magnet located at the outer end of the conductor member so as to direct a magnetic field into the conductor member;

and detecting changes in magnetic field in the metal body generated by the imperfections as the housing is moved in scanning movement along the metal body.

The term imperfections used herein is intended to include any changes in homogeneity of the metal body provided by cracks, pits, impurities, reductions in thickness for example caused by wear, poor weldments, and any other effects for which scanning of the body is required. The body can be a bar, rod, strap, tube, plate or any other shape of body including rectangular, circular.

By this arrangement there is provided a magnetic field sensor for detecting imperfections that is in a location where a substantial amount of magnetic flux is passing through and out of the metal body, as generated by the first and second magnets on either side of the sensor and the third magnet which is substantially aligned with the sensor generally in a radial direction from the metal body. Thus effectively the sensor is positioned in a path of the third magnet's magnetic field, with the conductor member acting to further focus or concentrate this magnetic field at the location where the sensor lies.

In one arrangement there is provided a plurality of conductor members and sensors at angularly spaced positions around a longitudinal axis of the housing extending along the metal body.

Preferably the magnets and the sensor are non-contact with respect to the metal body and therefore spaced from the metal body.

The magnets may be permanent magnets.

The sensor may be a Hall Effect sensor but other magnetic field sensors can be used.

The first magnet may be a first toroidal magnet arranged to surround the metal body, and the second magnet may be a second toroidal magnet arranged to surround the metal body.

The magnets each may be formed by a coil comprising a plurality of windings of wire arranged to be energized by an electric current for example DC current, a pulsing current, or a modulated frequency current that induces the magnetic field of the respective magnet.

Preferably the conductor member carries the third magnet at a position spaced outwardly from the metal body at a distance greater than that of the first and second magnets.

Preferably the sensor is located between the conductor member and the metal body.

The conductor member may be a ferromagnetic rod.

Preferably the first and second magnets have a magnetic pole immediately adjacent the metal body.

The housing is arranged to be carried in position over the elongate metal body defining a target of the scanning operation with or without a stand-off, that is a gap or space between the housing and the body. For example the housing may be carried in a manner held in wholly spaced relation from the surface of the body. Alternatively the housing may include rollers arranged for rolling engagement with the surface of the body.

A plurality of sensors may be arranged in an array on the forward end of the respective conductive member. The sensors are disposed in the array in a manner providing spatial information for example for defect imaging and speed encoding.

BRIEF DESCRIPTION OF THE DRAWINGS

Several arrangements of the invention will now be described in conjunction with the accompanying drawings in which.

In the drawings like characters of reference indicate corresponding parts in the different figures.

DETAILED DESCRIPTION

Figure 1:
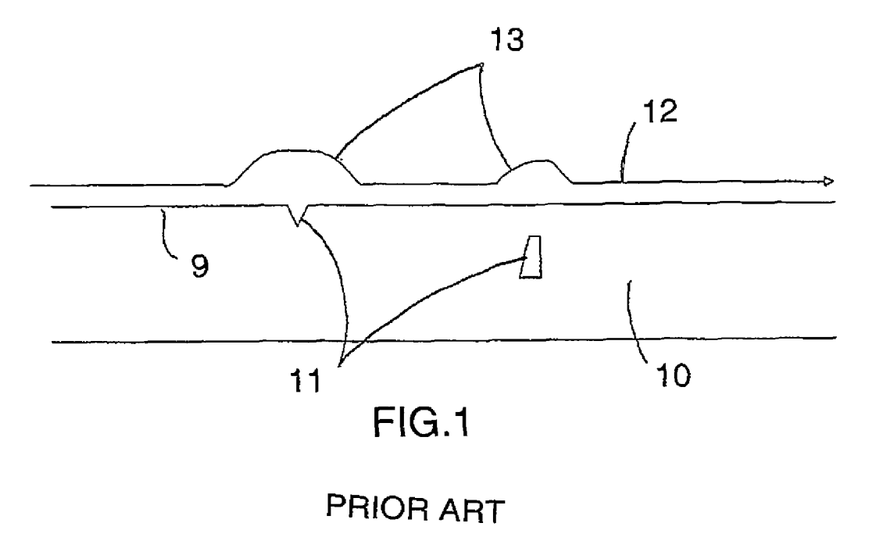
FIG. 1 is a prior art illustration of magnetic flux leakage caused by discontinuities within a test specimen.

The present invention is based on the concept that the magnetic field above the surface of a body of magnetizable material having a magnetic field induced therein will be of uniform flux except for where disturbed by the presence of discontinuities in the material, also known as imperfections or defects. This concept is illustrated in FIG. 1 where the magnetizable test material 10 is shown with an upper surface 9. The magnetic flux above the surface 9, indicated by a line 12 remains uniform, as illustrated by the straight sections of the line, except at points where discontinuities are present at or beneath the surface 9 of the material 10. The disturbances 13 above the discontinuities 11 constitute leakage flux which can be detected using sensors disposed in proximity to the surface 9 of the material 10. A flux leakage detection device utilizes a magnetizing device for providing a magnetic field in the test material and a magnetic field sensor for detecting leakage flux above the material's surface.

In FIGS. 2 to 5 is illustrated an apparatus generally indicated at 20 for detecting imperfections in an elongate metal body 10 defining the test material or target elongated in a longitudinal or axial direction of the body indicated at D. Several specific arrangements of this apparatus are shown all of which share the common features described below.

The apparatus 20 comprises a first pair of target magnetizing magnets 22, 23 (comprising a first magnet 22 and second magnet 23) which are supported at spaced locations with respect to the longitudinal or axial direction D and each in a position closely adjacent but spaced from the metal body 10 for applying a magnetic field in the body. As such each of the first and the second magnet has a magnetic pole 22A, 23A immediately adjacent the metal body so as to be facing an outer surface 10A thereof without any other portion of the apparatus in the line of sight between the respective one of these magnets and their magnetic field and the metal body.

Typically each of the first and second magnets has a pole of common polarity which is facing the target body 10.

Intermediate the first pair of target magnetizing magnets 22, 23 is a ferromagnetic or magnetizable conductor member 26 having a forward end 27A adjacent but spaced from the metal body 10 and which is elongated from the forward end 27A in a direction radially outwardly from an axis of the body or the longitudinal/axial direction D to an outer end 27B of the conductor.

A third target magnetizing magnet 29 is located at this outer end 27B of the conductor member with a magnetic pole 29A in abutment therewith that is of the common polarity of those poles of the first and second magnets facing the metal test body. The third magnet's magnetic field is directed into the conductor member 26 and passes through the metal body 10 so as to apply a magnetic field thereto. The conductor member 26 which forms a rod in the illustrated arrangements acts to focus or concentrate the magnetic field of the third magnet 29 particularly at the forward end 27A of the rod member over that distance between an end of the third magnet which is proximal to the metal body 10 and the body itself. The ferromagnetic conductor member 26 has an optimal length between its forward and outer ends so that the magnetic field is sufficiently focused at the forward end 27A with the appreciation that the greater the length of the conductor member 26 the more focussed is the magnetic field of the third magnet passing therethrough.

As the conductor member 26 is elongated and disposed between the third magnet 29 and the metal body 10 in the radial outward direction relative to the metal body 10 the third magnet 29 is located at a position spaced outwardly from the metal body at a distance greater than that of the first and second magnets 22, 23.

In the direct path of the third magnet's magnetic field focussed by the conductor member there is located a magnetic field sensor 32 such as a Hall Effect sensor at the forward end 27A of the conductor member. The sensor 32 is thus located so as to be intermediate the conductor member 26 and the metal body 10.

Magnetic field sensors of this type which are arranged to measure magnetic field are commercially available. Full details of the magnetic field sensor itself are not described in this application since the subject matter of this present application relates primarily to the mounting of the sensor relative to the target magnetizing magnets for detection of imperfections in the target body. The sensor is arranged in a manner so that a signal (typically a voltage) based on the strength of the measured magnetic field is output so that this signal can be analyzed to ascertain the presence of an imperfection.

The apparatus 20 includes a non-ferromagnetic housing 35 which supports at their prescribed positions the first through third target magnetizing magnets 22, 23 and 29, and the conductor member 26. As such the magnetic fields of the target magnetizing magnets can pass through the housing 35 in a manner which does not affect the flux of the magnetic field formed between the housing and the magnets and sensor and does not affect magnetization of the target body.

The housing 35 has a target side surface 37A for location in contact with or immediately adjacent to the outer surface 10A of the metal body for movement of the apparatus along the body in a scanning action. For example the housing may be carried on a track (not shown) holding the housing wholly in spaced relation to the metal body. Alternatively the housing may comprise rollers (made of non-ferromagnetic material) arranged to engage the outer surface of the metal body in rolling movement such that the housing is displaceable along the metal body while in contact therewith.

Adjacent a forward end 38A of the housing is located the first target magnetizing magnet 22 and adjacent a rearward end 38B of the housing is located the second target magnetizing magnet 23. Thus at a central location therebetween on the housing 35 is located the assembly of the conductor member 26 with the third magnet 29 at the outer end 27B distal to the metal body and the magnetic field sensor at the forward end 27A proximal and adjacent the body 10.

A conduit 39 of electrical wires carrying the signal output by the sensor 32 extends along the conductor member 26 from the forward end 27A at the sensor towards the outer end of the conductor member so that the signal can be analyzed and displayed by equipment externally of the housing.

Figure 2:
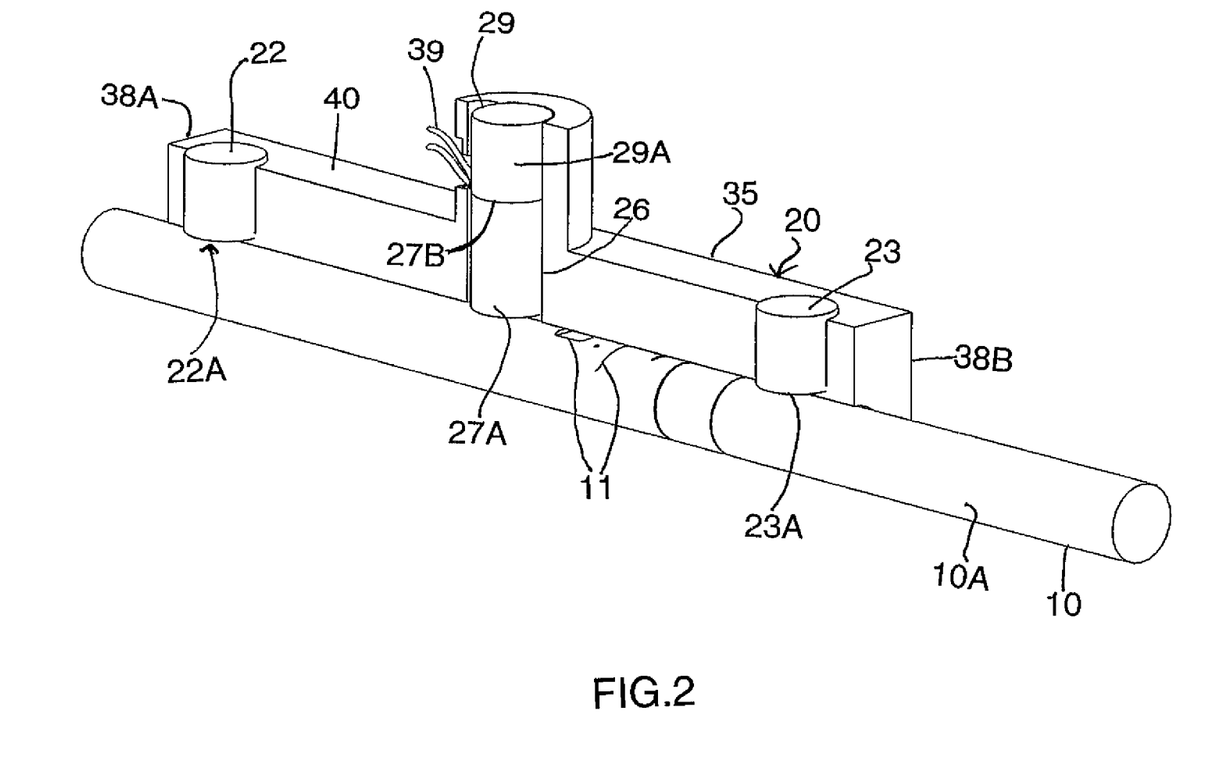
FIG. 2 is a perspective view of apparatus according to a first arrangement of the present invention where certain components are illustrated as partially transparent for clarity of illustration.

As shown in FIG. 2 the housing may comprise a unitary body 40 supporting each of the magnetizing magnets and the conductor rod. The unitary body means that those portions of the housing immediately surrounding and supporting the respective target magnetizing magnet form a single interconnected unit even though the housing may comprise separate sections which are fastened to one another.

Figure 3:
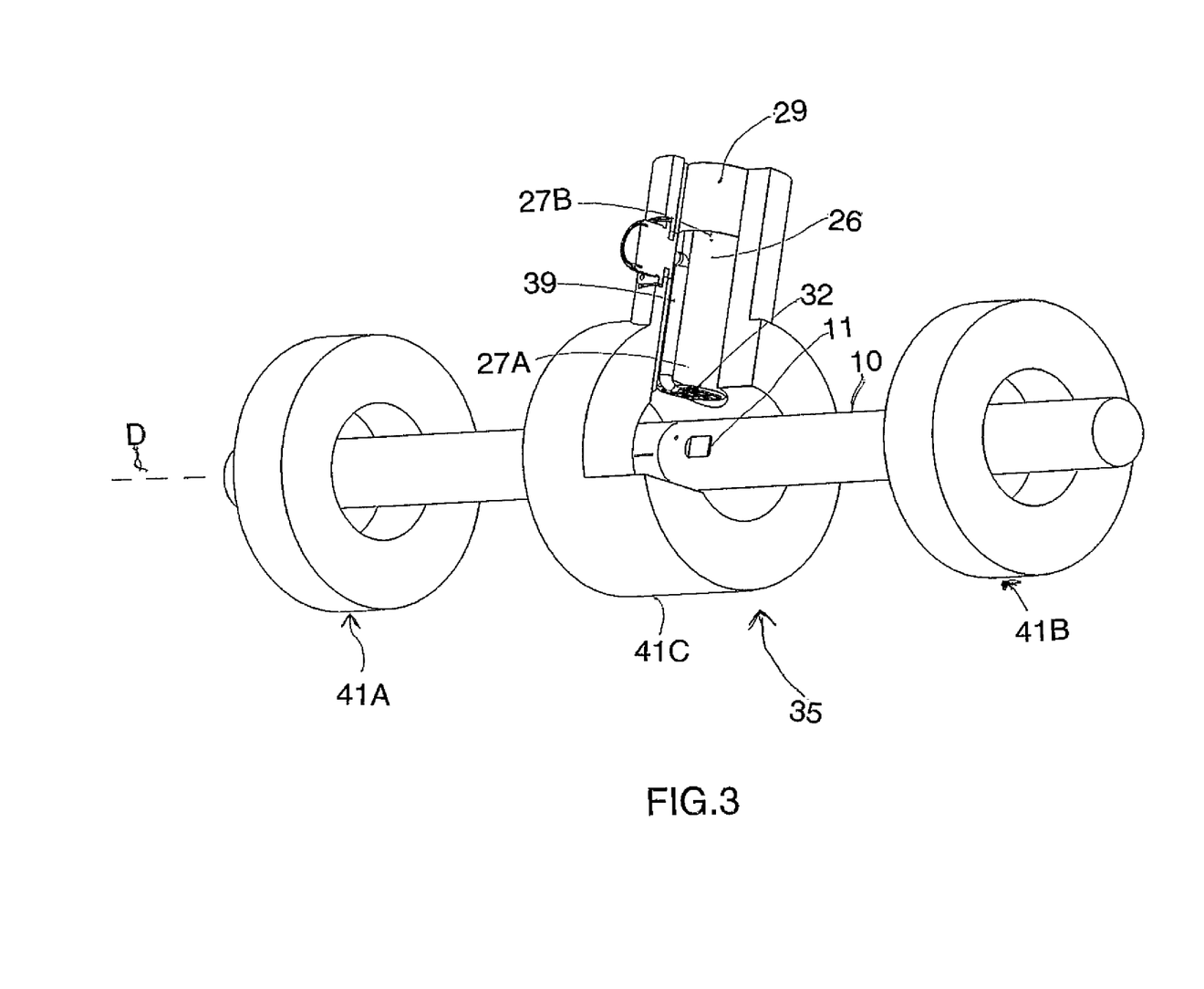
FIG. 3 illustrates an apparatus according to a second arrangement of the present invention where certain components are illustrated as partially transparent for clarity of illustration.
Figure 4:
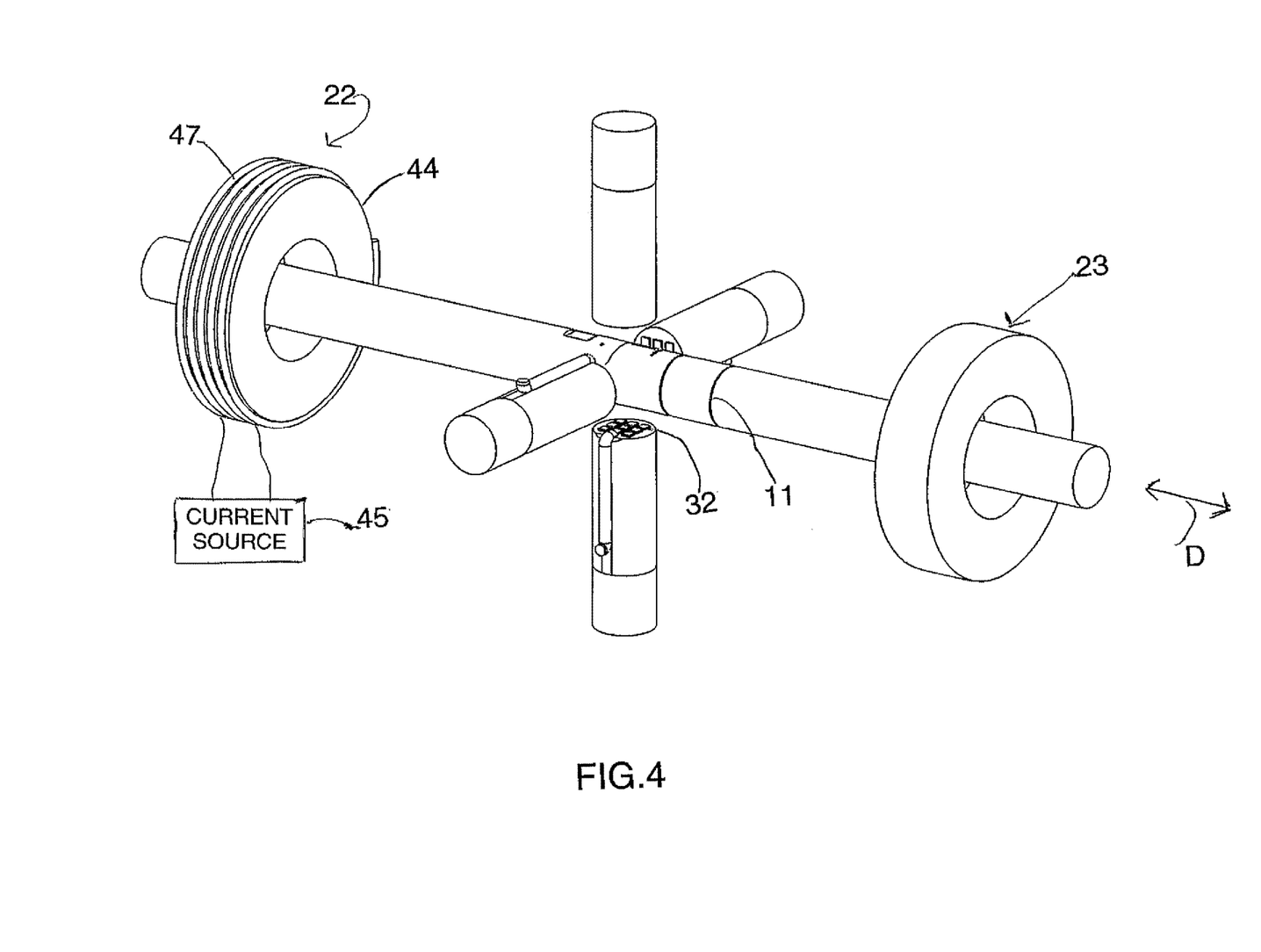
FIG. 4 illustrates an apparatus according to a third arrangement of the present invention where certain components are illustrated as partially transparent and others are omitted for clarity of illustration.

The housing may also be collectively formed by a plurality of separate housing segments 41A-41C which are indirectly linked together for example by being carried on a common track system (not shown) which moves the segments in unison (thereby maintaining the optimal spacing longitudinally of the metal body between the magnets and central sensor) along the metal body. As more clearly shown in FIG. 3 there may be for example a front housing segment 41A defining the forward end of the housing and which carries the first target magnetizing magnet; a central housing segment 41C spaced longitudinally rearwardly of the front segment that carries the third magnet-conductor member-sensor assembly; and a rear housing segment 41B carrying the second target magnetizing magnet that defines the rear end of the housing 35 and is spaced longitudinally rearwardly of the central segment along the metal body. In FIG. 3 each of the housing segments is toroidal so as to encompass a circumference or transverse periphery of the metal body.

The target side surface 37A may follow only a portion of a transverse periphery of the metal body as shown in FIG. 2. Alternatively the target side surface 37A may follow an entirety of the transverse periphery so as to encompass the metal body circumferentially thereof.

The magnets 22, 23 and 29 may be of a specific type and configured so as to direct their respective magnetic field primarily in a single radial direction relative to the longitudinal axis of the metal body. Typically in this arrangement the target magnetizing magnets are carried on the housing 35 so as to be located in a common radial plane containing the axis of the metal body. For example the magnets are permanent bar magnets disposed to one side of the metal body 10. Alternatively the magnets are electromagnetic coils 44 (schematically shown) energized by an electric current from a current source 45 (schematically shown) with respective coil axes, each of which extend through a plurality of windings or turns 47 (schematically illustrated) of wire forming the respective coil, oriented transversely to the axis of the metal body.

Particularly in regard to the first and second target magnetizing magnets, these magnets 22, 23 may be toroidal magnets each arranged to surround the metal body about its transverse periphery. In an arrangement where these magnets are formed by the energized coils the windings or turns of the coil may themselves encircle the metal body and the coil axis may be coaxial with the longitudinal axis of the body 10.

The electromagnetic coils 44 comprising the plurality of windings or turns 47 of wire are energized by the electric current 45 in order to form a magnetic field. This electric current may be for example a DC current which is intermittently interrupted or a modulated frequency current.

The magnetic field sensor may comprise a single sensor or a plurality of sensors arranged in an array at the forward end 27A of the conductor member 26. Thus the sensors arranged in the array are spaced each from the next and located at longitudinally spaced positions and/or at angularly spaced positions around a longitudinal axis of the housing which is parallel to that of the target body's axis and is extending along the metal body. Thus for example shown in FIG. 5 there is a 3×3 array individual sensors located at the front face of the magnetic conductor and closely adjacent the surface of the target.

In the illustrated arrangements the sensor occupies only a portion of an area of the forward end 27A of the conductor member so that a remaining portion of this area is exposed to the space between the housing and the metal body. Generally speaking presence of the sensor 32 at the forward end 27A of the housing does not substantially alter the magnetic field of the third magnet 29 that is directed through the conductor member 26.

Figure 5:
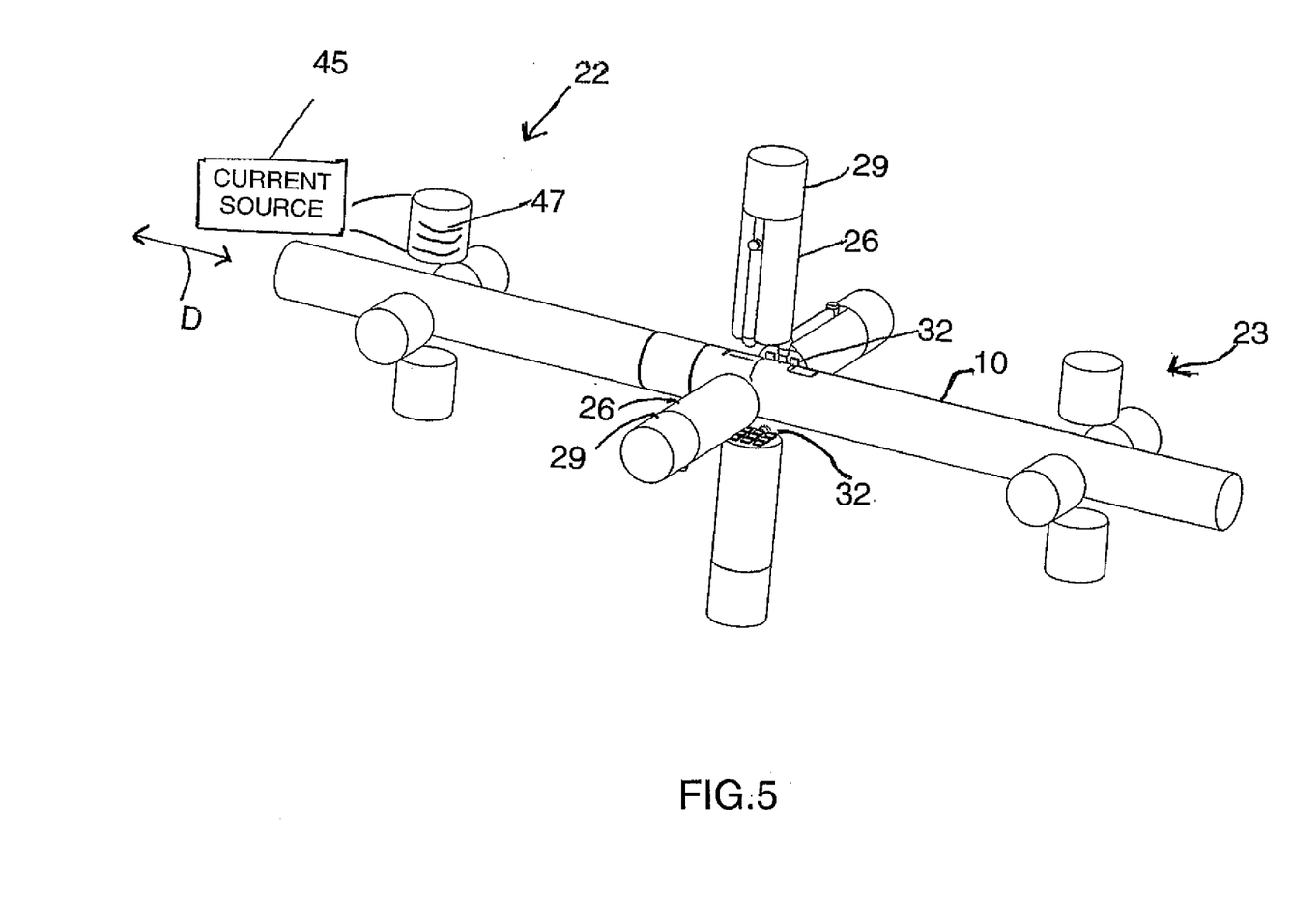
FIG. 5 illustrates an apparatus according to a fourth arrangement of the present invention where certain components are illustrated as partially transparent and others are omitted for clarity of illustration.

With the plurality of sensors arranged at angularly spaced positions about the axis of the metal body there is provided a plurality of the conductor members 26, as shown in FIG. 5, each of which has a set of the plurality of the sensors on its forward end 27A facing the target body's outer surface 10A. Each conductor member has at its outer end 27B a third magnetizing magnet so that there is a distinct assembly of the third magnet-conductor member-sensor at each angular location of the conductor relative to the metal body.

The apparatus 20 may be operated in a scanning method according to the following steps:

locating a first magnet 22 arranged on a housing 35 adjacent a forward end 38A of the housing at a position closely adjacent the metal body 10 so as to apply a magnetic field within in the body;

locating a second magnet 23 arranged on the housing adjacent a rearward end 38B of the housing at a position closely adjacent the metal body so as to apply a magnetic field within the body;

locating a ferromagnetic conductor member 26 on the housing 35 intermediate the first and second magnets having a forward end 27A adjacent the metal body and extending in a direction outwardly away from the metal body 10 to an outer end 27B;

locating a third magnet 29 located at the outer end 27B of the conductor member so as to direct a magnetic field into the conductor member 26;

and detecting changes in magnetic field in the metal body 10 generated by the imperfections 11 as the housing 35 is moved in the scanning movement along the metal body.

In performing a scanning action the apparatus 20 is positioned with its target side surface 37A facing the outer surface 10A of the body so that a longitudinal axis of the housing is parallel to the axis of the body D and located in a radial plane of containing the body axis. (Typically the longitudinal axis of the housing will be coaxial to that of the metal body 10.) With each of the first through third magnets 22, 23, and 29 applying their respective magnetic field to the metal body so as to induce a magnetic field therein, the housing 35 is displaced in scanning movement along the metal body during which the sensor 32 detects changes in the magnetic field adjacent the outer surface 10A of the body in a space between same and the forward end 27A of the conductor member. More specifically the Hall Effect sensor detects changes in flux of in the magnetic field passing through this localized space between the metal body and the sensor that arise from imperfections in the body.

When a plurality of the sensors are provided at angularly spaced positions spatial information of the body may be obtained for generating an image of the test material and any imperfections therein. In an arrangement of the apparatus such as that illustrated in FIG. 2 where the sensor is provided at a common angular position relative to the body, the housing may be rotated about a pivot axis defined by the longitudinal axis of the body so as to provide spatial information about the metal body 10.

Since various modifications can be made in my invention as herein above described, and many apparently widely different embodiments of same made, it is intended that all matter contained in the accompanying specification shall be interpreted as illustrative only and not in a limiting sense.

The invention claimed is:

1. A method for detecting imperfections in an elongate metal body comprising:
   locating a first magnet arranged on a housing adjacent a forward end of the housing at a position closely adjacent the elongate metal body so as to apply a magnetic field within the elongate metal body;
   locating a second magnet arranged on the housing adjacent a rearward end of the housing at a position closely adjacent the elongate metal body so as to apply a magnetic field within the elongate metal body;
   locating a ferromagnetic conductor member on the housing intermediate the first and second magnets having a forward end adjacent the elongate metal body and extending in a direction outwardly away from the elongate metal body to an outer end;
   locating a third magnet located at the outer end of the ferromagnetic conductor member so as to direct a magnetic field into the ferromagnetic conductor member;
   providing at least one magnetic field sensor located at the forward end of the ferromagnetic conductor member;
   and using the magnetic field sensor to detect changes in magnetic field in the elongate metal body generated by the imperfections as the housing is moved in scanning movement along the elongate metal body.

2. The method according to claim 1 wherein the magnetic field sensor detects changes in magnetic field in the elongate metal body generated by the imperfections as the housing is moved in scanning movement along the elongate metal body.

3. The method according to claim 1 wherein there is provided a plurality of ferromagnetic conductor members and a plurality of magnetic field sensors at angularly spaced positions around a longitudinal axis of the housing extending along the elongate metal body.

4. The method according to claim 1 wherein the first, second and third magnets are permanent magnets.

5. The method according to claim 1 wherein the said at least one magnetic field sensor is a Hall Effect sensor.

6. The method according to claim 1 wherein the said at least one magnetic field sensor is an array of individual magnetic field sensors.

7. The method according to claim 1 wherein the first magnet is a first toroidal magnet arranged to surround the elongate metal body and the second magnet is a second toroidal magnet arranged to surround the elongate metal body.

8. The method according to claim 1 wherein the first magnet is one of a plurality of first magnets arranged at angularly spaced positions around the elongate metal body to surround the elongate metal body and the second magnet is one of a plurality of second magnets arranged at angularly spaced positions around the elongate metal body.

9. The method according to claim 1 wherein the first, second and third magnets each are formed by a coil comprising a plurality of windings of wire arranged to be energized by an electric current such that the coil induces the respective magnetic field.

10. The method according to claim 1 wherein the ferromagnetic conductor member carries the third magnet at a position spaced outwardly from the elongate metal body at a distance greater than that of the first and second magnets.

11. The method according to claim 1 wherein the ferromagnetic conductor member is a ferromagnetic rod.

12. The method according to claim 1 wherein the first and second magnets have a magnetic pole immediately adjacent the elongate metal body.

13. The method according to claim 1 wherein said at least one magnetic field sensor comprises a plurality of magnetic field sensors arranged in an array on the forward end of the ferromagnetic conductor member.

\* \* \* \* \*